United States Patent [19]

Eggers et al.

[11] Patent Number: 5,630,426

[45] Date of Patent: May 20, 1997

[54] APPARATUS AND METHOD FOR CHARACTERIZATION AND TREATMENT OF TUMORS

[75] Inventors: Philip E. Eggers, Dublin, Ohio; Ascher Shmulewitz, Mercer Island, Wash.

[73] Assignee: NeoVision Corporation, Seattle, Wash.

[21] Appl. No.: 398,644

[22] Filed: Mar. 3, 1995

[51] Int. Cl.$^6$ ............................... A61B 5/05; A61N 1/05
[52] U.S. Cl. ........................ 128/734; 128/642; 606/34; 606/41; 607/99; 607/113
[58] Field of Search ................................ 128/734, 642; 607/98, 99, 113; 606/21, 27, 28, 30, 41, 49, 50, 34

[56] References Cited

U.S. PATENT DOCUMENTS

| | | | |
|---|---|---|---|
| Re. 34,421 | 10/1993 | Parker et al. | 378/121 |
| 4,016,886 | 4/1977 | Doss et al. | 128/422 |
| 4,121,592 | 10/1978 | Whalley | 128/413 |
| 4,140,109 | 2/1979 | Savic et al. | 128/2.1 Z |
| 4,291,708 | 9/1981 | Frei et al. | 128/734 |
| 4,458,694 | 7/1984 | Sollish et al. | 128/734 |
| 4,520,249 | 5/1985 | Czerlinski | 219/10.49 R |
| 4,658,836 | 4/1987 | Turner | 128/804 |
| 4,679,561 | 7/1987 | Doss | 128/422 |
| 4,737,628 | 4/1988 | Lovoi | 250/226 |
| 4,821,725 | 4/1989 | Azam et al. | 128/420 |
| 4,846,196 | 7/1989 | Wiksell et al. | 128/784 |
| 4,860,744 | 8/1989 | Johnson et al. | 128/303.1 |
| 4,872,458 | 10/1989 | Kanehira et al. | 128/401 |
| 4,919,138 | 4/1990 | Nordenstroöm | 128/421 |
| 4,920,978 | 5/1990 | Colvin | 128/784 |
| 4,979,518 | 12/1990 | Itoh et al. | 128/785 |
| 5,069,223 | 12/1991 | McRae | 128/734 |
| 5,122,137 | 6/1992 | Lennox | 606/40 |
| 5,143,079 | 9/1992 | Frei et al. | 128/734 |
| 5,251,645 | 10/1993 | Fenn | 607/154 |
| 5,284,144 | 2/1994 | Delannoy et al. | 128/653.2 |

FOREIGN PATENT DOCUMENTS

| | | | |
|---|---|---|---|
| 0249631 | 9/1987 | Germany | 606/49 |
| 3930451 | 3/1991 | Germany | 128/734 |

OTHER PUBLICATIONS

Savic, M. and Zacarian, S.A., "A New Impedance–Based Method for Controlled Cryosurgery of Malignant Tumors", *The Journal of Dermatologic Surgery and Oncology*, Nov./Dec. 1977, pp. 592–593.

Abele, J.S., et al., "Fine–Needle Aspiration of Palpable Breast Masses", *Arch. Surgery*, Jul. 1983, pp. 859–863.

Morimoto, T., et al., "Measurement of the Electrical Bio-–Impedance of Breast Tumors", *European Surgery Research*, 1990, pp. 86–92.

*Primary Examiner*—Lee S. Cohen
*Attorney, Agent, or Firm*—Fish & Neave; Nicola A. Pisano

[57] ABSTRACT

Apparatus and methods are provided for performing an in situ characterization of a tissue mass which may be normal, malignant, or benign, and, based on the measured characteristics of the tissue mass, therapeutically treating the tissue mass to cause necrosis of the tissue. In an illustrative preferred embodiment, the characterization of the tissue is accomplished by measuring an electrical property of the tissue, such as electrical impedance, while treatment is accomplished by supplying heat to the tissue to induce cauterization.

35 Claims, 8 Drawing Sheets

APPARATUS AND METHOD FOR CHARACTERIZATION AND TREATMENT OF TUMORS

FIELD OF THE INVENTION

The present invention relates to apparatus and a method for performing in situ characterization of the cancerous nature of biological tissue and in situ necrosis of biological tissue.

BACKGROUND OF THE INVENTION

Apparatus and methods are known to identify, in situ, tumorous masses in biological tissue by using the electrical properties of such tissue, for example, by determination of electrical impedance or dielectric constants. It is also known that some benign and malignant tumors may be determined from differences in the measured electrical properties of such tissue.

It has been reported, for example, in T. Morimoto, et al., "Measurement of the Electrical Bio-Impedance of Breast Tumors," *European Surgical Research*, Vol. 22, pg. 86–92 (1990), that there are measurable differences between the electrical impedances of normal breast tissue, benign breast tumors, and malignant breast tumors. That paper describes a coaxial electrode arrangement wherein current pulses are conducted from an outer conductor of the electrode to a ground plate while voltage between an inner conductor of the electrode and the ground plate is sensed to determine tissue impedance.

Apparatus and methods are also known for causing in situ necrosis of tumorous masses, such as by hyperthermia (raising the temperature of biological tissue through inductive, radiant, contact, and joulean heating methods), the use of ionizing radiation (e.g., X-ray therapy), and cryosurgery. Several such devices are described in U.S. Pat. No. 4,016,886 and 4,121,592 (hyperthermia); Re 34,421 (ionizing radiation); and U.S. Pat. No. 4,140,109 (cryosurgery).

It is further known, for example by McRae U.S. Pat. No. 5,069,223, that the electrical impedance of an identified tissue mass may be measured to determine the progress resulting from hyperthermic treatment. McRae describes an electrode-bearing probe that may be inserted into biological tissue to sense the change in electrical impedance induced by a separate heating applicator.

A drawback of the above-described previously known apparatus and methods is that a first device is used for characterizing the biological tissue (e.g., whether tissue is malignant or nonmalignant) and a second, separate, device is then required for treating the tissue. For example, the device described in the Morimoto reference may be used to identify a tumorous tissue mass. The identified tissue mass may then be treated, for example, by hyperthermia, by positioning a treatment device at the proper location and actuating it. Finally, a method such as described in the McRae patent may be used to sense the electrical impedance of the tissue exposed to hyperthermia to monitor the progress of the therapeutic treatment.

Since the step of characterizing a target tissue is performed independently of the step of positioning the treatment device, within or adjacent to that tissue, previously known apparatus and methods do not provide accurate registration between the measuring device and the treatment device. Consequently, the potential arises for incompletely treating the intended tissue mass, thus leaving intact tumorous cells, or alternatively causing extensive necrosis to healthy tissue to avoid incomplete treatment. Moreover, these previously known techniques and devices are excessively invasive and the sequential or combined nature of their use may result in significant patient discomfort.

In view of the foregoing, it would be desirable to provide apparatus and methods in which a single instrument is used both to characterize and to treat tumors in situ. The ability to characterize and treat tumors with a single instrument would significantly reduce the invasiveness required in the characterization and treatment of tumors in accordance with previously known apparatus and methods.

It would also be desirable to provide apparatus and methods for conducting in situ characterization and treatment of tissue, using a single device, to improve the efficiency of the medical procedure and to reduce patient distress during the medical procedure.

It would also be desirable to provide apparatus and methods for in situ characterization and treatment of tissue that provides a high degree of registration between the measuring apparatus and the treatment apparatus, thereby providing the ability to treat tissue adequately without excessive damage to neighboring healthy tissue.

SUMMARY OF THE INVENTION

In view of the foregoing, it is an object of this invention to provide a apparatus and methods capable of both (1) characterizing, in situ, whether a tumor or tissue mass is normal, malignant, or nonmalignant and (2) inducing necrosis, in situ, of any tumor that is suspected to be malignant.

It is another object of this invention to achieve both a characterization of degree of malignancy and treatment of the tumor with a single instrument brought into direct contact with or adjacent to the thus improving the efficiency of the medical procedure and reducing patient distress during the medical procedure.

It is yet another object of the present invention to provide apparatus and methods for in situ characterization and treatment of suspected malignant tissue that provides a high degree of registration between the measuring apparatus and the treatment apparatus, thereby providing the ability to treat tissue adequately without excessive damage to neighboring healthy tissue.

It is a still further object of the present invention to provide apparatus and methods for causing tumor necrosis during a brief period of time (e.g., several seconds to tens of seconds), where such apparatus and methods are compatible with existing noninvasive tumor-imaging techniques.

These and other objects of the invention are accomplished in accordance with the principles of the invention by providing apparatus and methods for in situ characterization and treatment of tumors that enables the user both to measure one or more electromagnetic properties of biological tissue to characterize the degree of malignancy of the tumor (e.g., based on the vascularity of the tumor mass), and then to cause necrosis of biological tissue if it is determined that treatment is appropriate.

The apparatus of the present invention utilizes the measurable differences in one or more electromagnetic properties (e.g., electrical impedance) of normal, malignant, and nonmalignant tissue to (1) discriminate, in situ, between malignant and nonmalignant tissue and (2) assess degree of malignancy, and (3) to treat, in situ, by inducing tumor necrosis through, e.g., inducing elevated temperatures in the tissue (i.e., cauterization or hyperthermia).

Further features of the invention, its nature and various advantages will be more apparent from the accompanying drawings and the following detailed description of the preferred embodiments.

DETAILED DESCRIPTION OF THE PREFERRED EMBODIMENTS

The present invention relates generally to apparatus having both diagnostic means, for characterizing whether a tissue mass is malignant or nonmalignant, and treatment means, for causing necrosis of the tissue mass if it is suspected of being malignant. In the exemplary embodiment of the apparatus and methods of the invention described hereafter, characterization of tumor type (e.g., either malignant or nonmalignant, as well as degree of virulence of malignancy based on vascularity) is based on determining the electrical impedance, or resistance, of biological tissue, while necrosis of the biological tissue is illustratively accomplished by inducing elevated temperatures in the tissue.

It will of course be understood by those skilled in the relevant arts that these exemplary embodiments of the invention in no way limit the intended use of the apparatus and methods of the present invention, and that other characterizing parameters, such as dielectric constant, and other treatment modalities, such as cryogenic or ionizing radiation, may also be utilized within the scope and spirit of the present invention.

Figure 1:
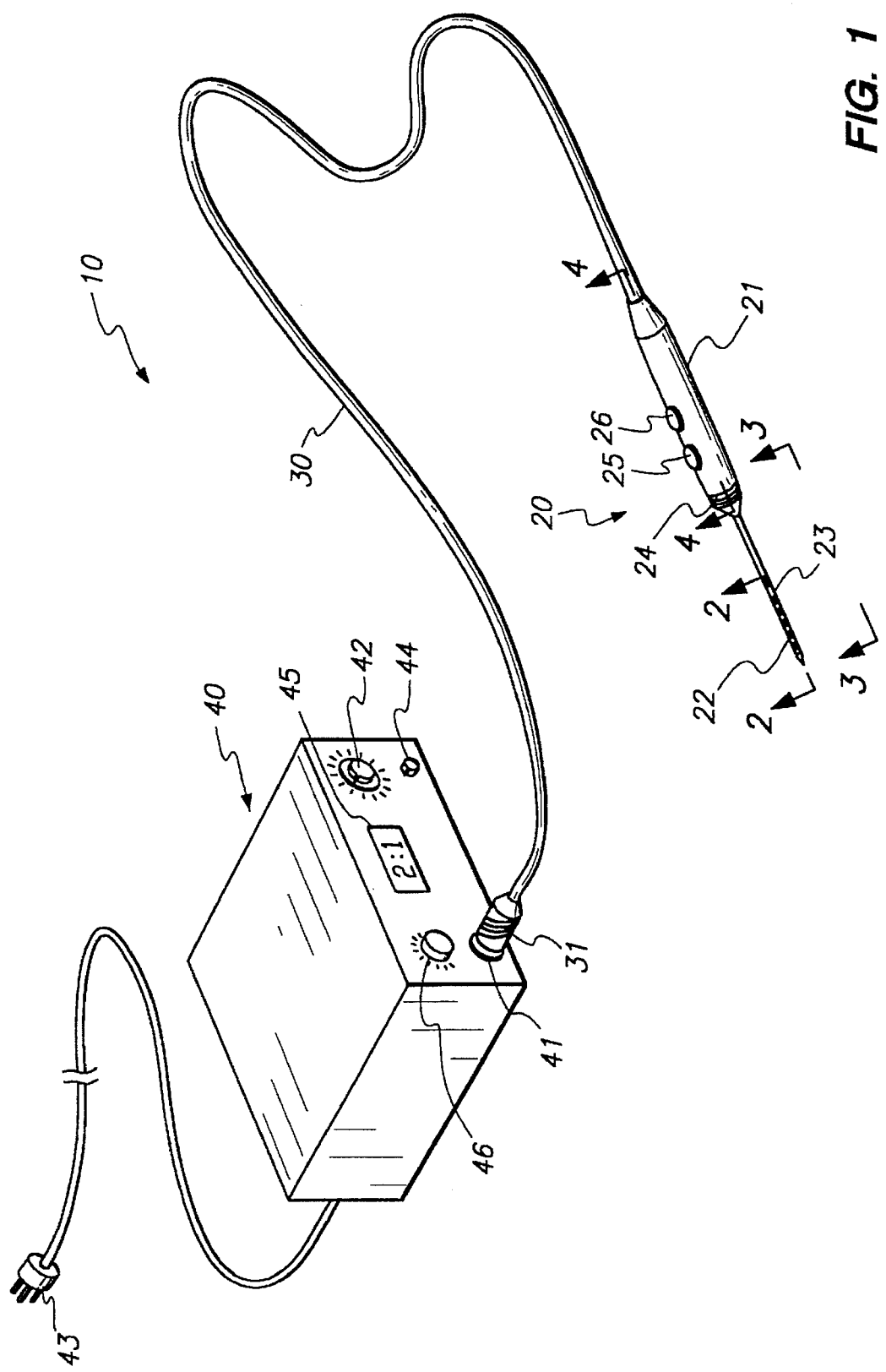
FIG. 1 is a perspective view of a first illustrative embodiment of the measurement and treatment probe, control system, and connecting cable of the present invention.

Referring to FIG. 1, a first illustrative embodiment of apparatus 10 of the present invention comprises measurement and treatment probe 20, cable 30 and controller 40.

Measurement and treatment probe 20 (hereinafter referred to as the "probe") has hand-engagable handle 21 at its proximal end and carries both diagnostic treatment means and therapeutic treatment means at its distal end 22. Distal portion 22 includes a plurality of electrodes for use in the measurement of at least one electromagnetic property (e.g., electrical impedance) of biological tissue and application of heating current to the target biological tissue, as described in detail below.

Probe 20 further includes shaft 23 removably coupled to handle 21 by connector 24. Handle 21 may include manual measurement control 25 and manual therapy control 26 for actuating the measurement and treatment modes of operation, respectively. Alternatively, handle 21 may include a three position slide or rocker-type switch instead of controls 25 and 26, or these functions may be instead incorporated in a foot-pedal type switch.

Controller 40 is connected to handle 21 of probe 20 via cable 30. Cable 30 includes the electrically conducting leads necessary for the transmission of measurement signals, heating currents and switch control signals between probe 20 and controller 40. Controller 40 has circuitry that energizes probe 20 during use in both diagnostic and therapeutic modes of operation. Port 41 is provided on the faceplate of controller 40 for accepting connector 31 of cable 30, while graduated dial or knob 42 is provided to adjust the power level applied to probe 20. Controller 40 connects to a conventional 110–120 V 60 Hz power supply via plug 43 and is turned on and off using switch 44.

Controller 40 also may include sensory display 45 to indicate a value indicative of the measured electrical property (in diagnostic mode) or output voltage (in therapeutic mode). Sensory display 45 may be, e.g., an audible indicator or a visual indicator such as a CRT or a recording device. Sensory display 45 may also include an audible tone having a frequency (i.e., pitch) that corresponds to the value of the measured electrical property. The audible tone volume may be adjusted using dial 46.

In a preferred embodiment of the apparatus of FIG. 1, the proximal end of cable 30 is removably connected to controller 40 using cable connector 31, while the distal end of cable 30 may be removably coupled to, or integral with, probe handle 21. Cable 30 and handle 21 may be resterilized and reused multiple times. Alternatively, these components may be formed of inexpensive, lightweight material (e.g., injection molded plastic) and therefore be completely disposable. Distal end 22 and shaft 23 may also be disposable and may have a variety of lengths, diameters and electrode arrangements to accommodate a variety of applications as required by the physiological differences in the size and location of the tumor being characterized and treated.

Figure 2:
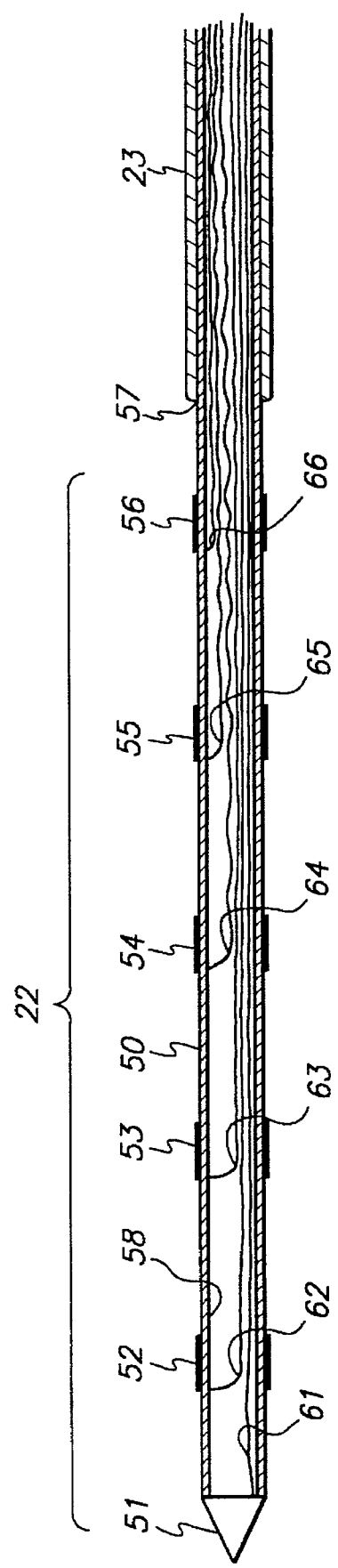
FIG. 2 is a cross-sectional view of the measurement and treatment probe of FIG. 1, taken along the line 2—2 of FIG. 1.
Figure 3:
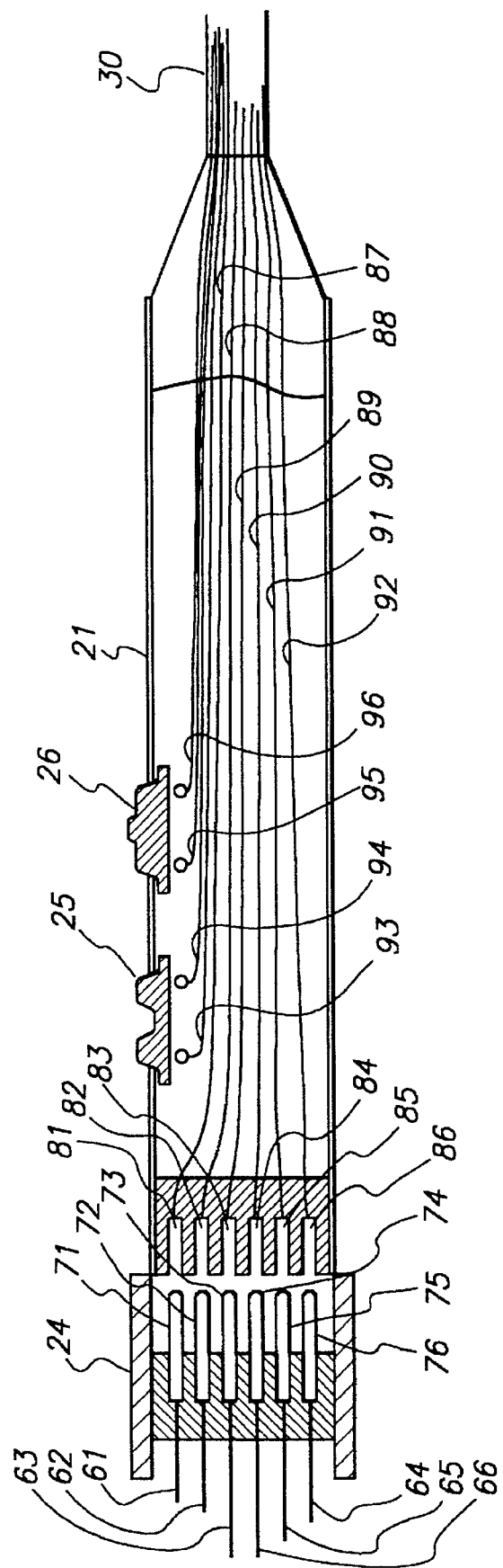
FIG. 3 is a cross-sectional view of the measurement and treatment probe of FIG. 1, taken along line 4—4 of FIG. 1.

Referring now to FIGS. 2 and 3, the construction of distal end 22 and handle 21 of probe 20 of the first illustrative embodiment of the present invention is described. As shown in FIG. 2, distal end 22 of probe 20 includes a plurality of circumferential electrodes 51 through 56 disposed on support member 50. Each electrode 51 through 56 is electrically insulated from the others and from support member 50. Electrodes 51–56 comprise a suitable bio-inert material, for example, platinum, silver, gold or stainless steel, having a thickness in a range of 0.1 to 5.0 mils (0.002 to 0.13 mm). Electrodes 51–56 are spaced apart axially along support member 50 at intervals which may vary according to the intended application of probe 20.

Support member 23 may be constructed of a flexible or rigid electrically nonconductive material, or alternatively, may be constructed from a metallic tube (e.g., stainless steel Type 304) covered by a thin electrically insulative coating, for example, a polymeric shrink tubing, or a thin layer of organic or inorganic electrically insulative material. Support element 50 of distal portion 22 may be inserted through bore 57 of shaft 23, thereby providing additional mechanical support for support member 50. Support member 50 includes central bore 58 for routing lead wires to each of electrodes 51–56.

Referring now also to FIG. 3, each electrode 51 through 56 is connected to lead wire 61 through 66, respectively. Lead wires 61–66 are electrically insulated from one another by a suitable electrically insulative coating, e.g., a polymeric covering. Each lead wire 61–66 terminates in pins 71 through 76 electrically insulated from each other in connector 24. Pins 71–76 engage contacts 81 through 86, respectively, disposed at the distal end of handle 21. Contacts 81–86 are electrically connected to lead wires 87 through 92, respectively, which extend through cable 30 and are coupled to controller 40 (see FIG. 1). Additional lead wires 93 through 96 allow the actuation of manual controls 24 and 25 on handle 21 to be detected by controller 40 to energize the probe for either diagnostic or therapeutic modes of operation.

In a preferred embodiment of the illustrative apparatus of FIG. 1, support member 50 has a length and diameter suitable for allowing access to tumors in the human body, such as breast tumors. By way of example, support member 50 of distal end 22 of probe 20 may have a diameter of about 1 mm and a length of 10 cm or longer. Tissue impedance measurements are conducted in the diagnostic mode of operation by conducting a low voltage radio-frequency current between outermost electrodes 51 and 56, while electrode pairs 52, 53 and 54, 55 are used to sense the voltage drop through the tissue along the length of support member 50, as described in detail below.

Once the tissue type has been characterized (e.g., by degree of vascularity of the tumor), the tumor is treated by passing current through electrode pair 52 and 53. Lead wires 62 and 63 are preferably of a larger diameter (e.g., 0.1 to 0.25 mm) than lead wires 61 and 62–66 because while lead wires 61 and 64–66 conduct only low voltages or currents used in the diagnostic mode, lead wires 62 and 63 carry both low voltages and currents during the diagnostic mode as well as higher voltages and currents during the therapeutic mode.

Figure 4:
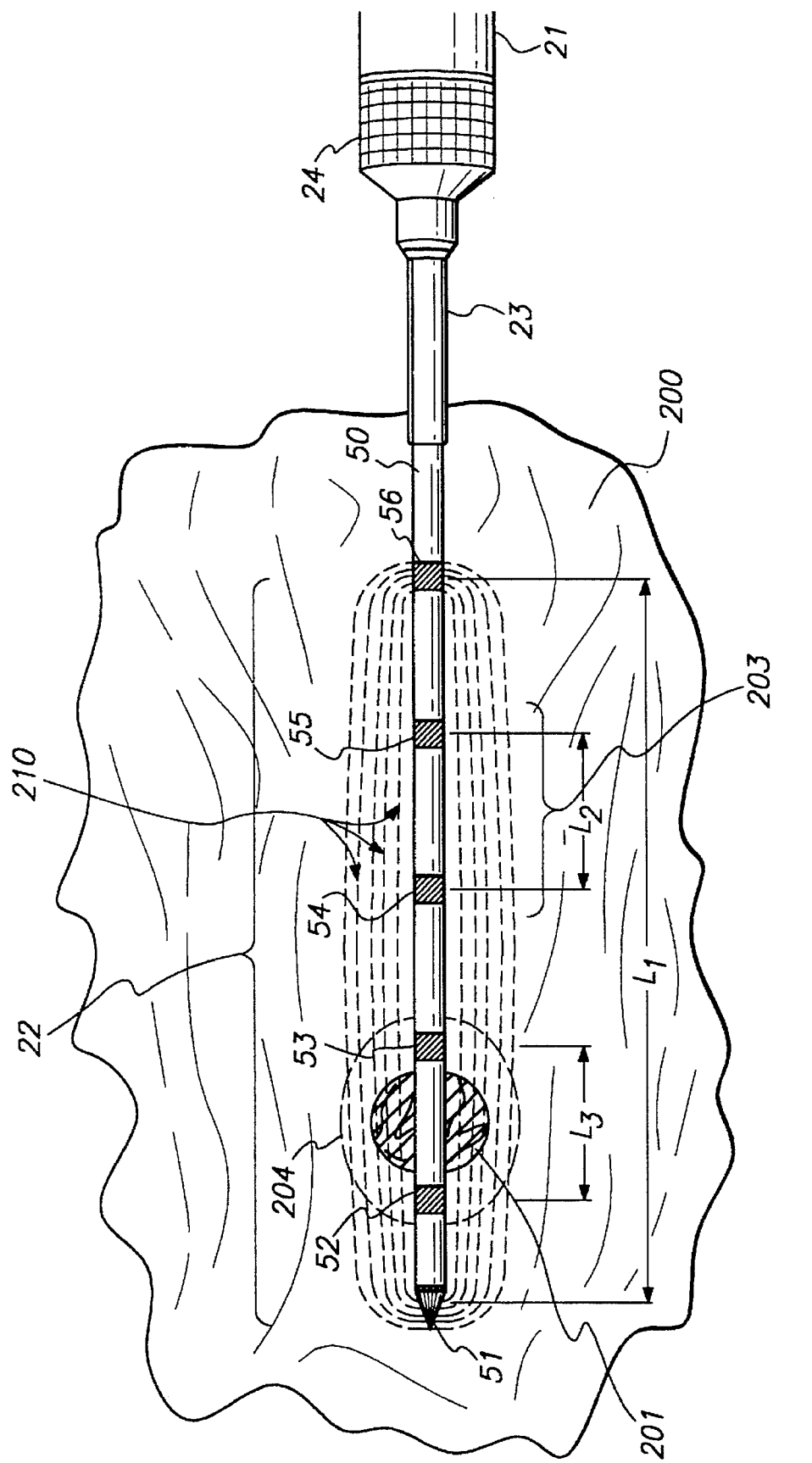
FIG. 4 is a side view of the measurement and treatment probe of FIG. 1, taken along the line 3—3, showing the probe inserted into biological tissue.

Operation of the apparatus of FIG. 1 is now described with respect to FIG. 4 and the methods of the present invention. As shown in FIG. 4, distal portion 22 of support member 23 is inserted into the patient percutaneously so that distal portion 22 is positioned in close proximity to (or within) tumor 201. Distal portion 22 may be guided to the location of a targeted tissue mass using the coordinates, targeted tissue mass size and orientation determined in previous X-radiographic, sonographic, or other diagnostic imaging procedures.

Once distal portion 22 is properly positioned relative to the targeted tissue mass, manual measurement control 25 (see FIG. 3) is depressed to activate measurement of an electromagnetic property of the targeted tissue mass and adjacent normal tissue. In particular, when manual measurement control 25 is depressed controller 40 applies a low voltage (e.g., less than about 10 volts) radio-frequency current (e.g., from 20 kHz to 20 MHz) across the outermost pair of electrodes 51 and 56. This current is indicated by flux lines 210 in FIG. 4. An indication corresponding to the measured electromagnetic property of the tissue mass, or a ratio of the measured tissue mass property to the measured normal tissue property, is then provided, as described below.

The voltage applied between electrodes 51 and 56 for purposes of measuring tissue impedance may be selected based upon several factors, including (1) the distance $L_1$ between electrodes 51 and 56, (2) the upper limit of the current level to maintain a desired maximum tissue heating (e.g., less than 2° C.), and (3) the lower limit of the current level necessary to allow accurate measurement of the properties of the tumor 201 and the normal tissue 200 in region 203. Thus, the applied radio-frequency voltage between electrodes 51 and 56 may typically be less than 10 volts and, more preferably, between 2 to 4 volts, and may be controlled by a predetermined current limit set in controller 40. The property measurements also may be made at several frequencies, preferably within the range 20 kHz to 20 MHz, to facilitate discrimination of tissue type.

During the period of low level current flow between electrodes 51 and 56, the voltage difference between electrode pairs 52 and 53 and electrode pair 54 and 55 is measured by circuitry within controller 40, for example, voltmeter circuitry or a bridge circuit. By selecting the interelectrode spacing $L_3$ between electrodes 52 and 53 to be the same as the interelectrode spacing $L_2$ between electrodes 54 and 55 (see FIG. 4), the measured voltages between electrodes 52 and 53 and electrodes 54 and 55 may be directly compared to assess the difference in electrical properties in the two regions.

For example, the electrical impedance of tumor 201 and normal tissue 200 in region 203 may be calculated based on (1) the measured current flowing between electrodes 51 and 56, (2) the measured voltage difference between electrode pairs 52/53 and 54/55, respectively, and (3) the interelectrode spacing $L_2$ and $L_3$ between these electrode pairs. Alternatively, the measured electrical property may be represented as a ratio of the voltage differences between electrode pairs 52/53 and 54/55.

If interelectrode spacings $L_2$ and $L_3$ are equal and the total electrical current flowing through tissue adjacent to each of electrode pairs 52/53 and 54/55 is also equal, the ratio of measured voltages between electrode pairs 52/53 and 54/55 represents the ratio of electrical impedance of tissue in the region of the tumor 201 and normal tissue 200 in region 203, respectively. This measured ratio may be indicated by sensory display 45 of controller 40 (see FIG. 1).

If the operator then translates distal portion 22 forward and backward in tissue 200, the displayed ratio and/or audible tone frequency of sensory display 45 will vary, thus indicating the position of electrodes 52 and 53 relative to tumor 201. Moreover, by comparing the parameter value indicated on sensory display 45 to a table of predetermined values, it is possible for the operator to characterize the tissue being measured. This is accomplished, for example, by measuring the difference in electrical impedance between tissue known to be normal and tissue suspected of being malignant.

Upon completing the assessment as to the malignancy of tumor 201, the operator may either (1) withdraw distal portion 22 from the tissue or if the assessment indicates the tumor should be treated, (2) depress manual therapy control 26 (see FIG. 3) until the desired thermal treatment (e.g. tissue cauterization) is accomplished. When therapy control 26 is depressed controller 40 applies a sufficiently high radio-frequency voltage (e.g., 10–100 volts RMS between 100 kHz and 1 MHz, preferably 350–500 kHz) across electrodes 52 and 53 to effect heating and cauterization of biological tissue located in the region 204 located between electrodes 52 and 53. In general, applicants expect that only a few seconds will be required to raise the temperature of the targeted tissue to a range of 60° C. to 100° C., thereby causing necrosis of the tissue. Once application of the treatment current has been completed, distal end 22 of probe 20 is withdrawn from the patient's tissue.

Optionally, a thermistor may be disposed on or within distal end 22, and in communication with temperature-sensing circuitry in controller 40, to monitor the heating of the biological tissue in region 204. Preferably, the temperature of the biological tissue in region 204 is kept below a temperature at which the cauterization process causes the evolution of steam from the desiccating biological tissue, for example, less than about 100° C. Alternatively, probe 20 may include means for venting any vapors produced by heating of the biological tissue.

Figure 5:
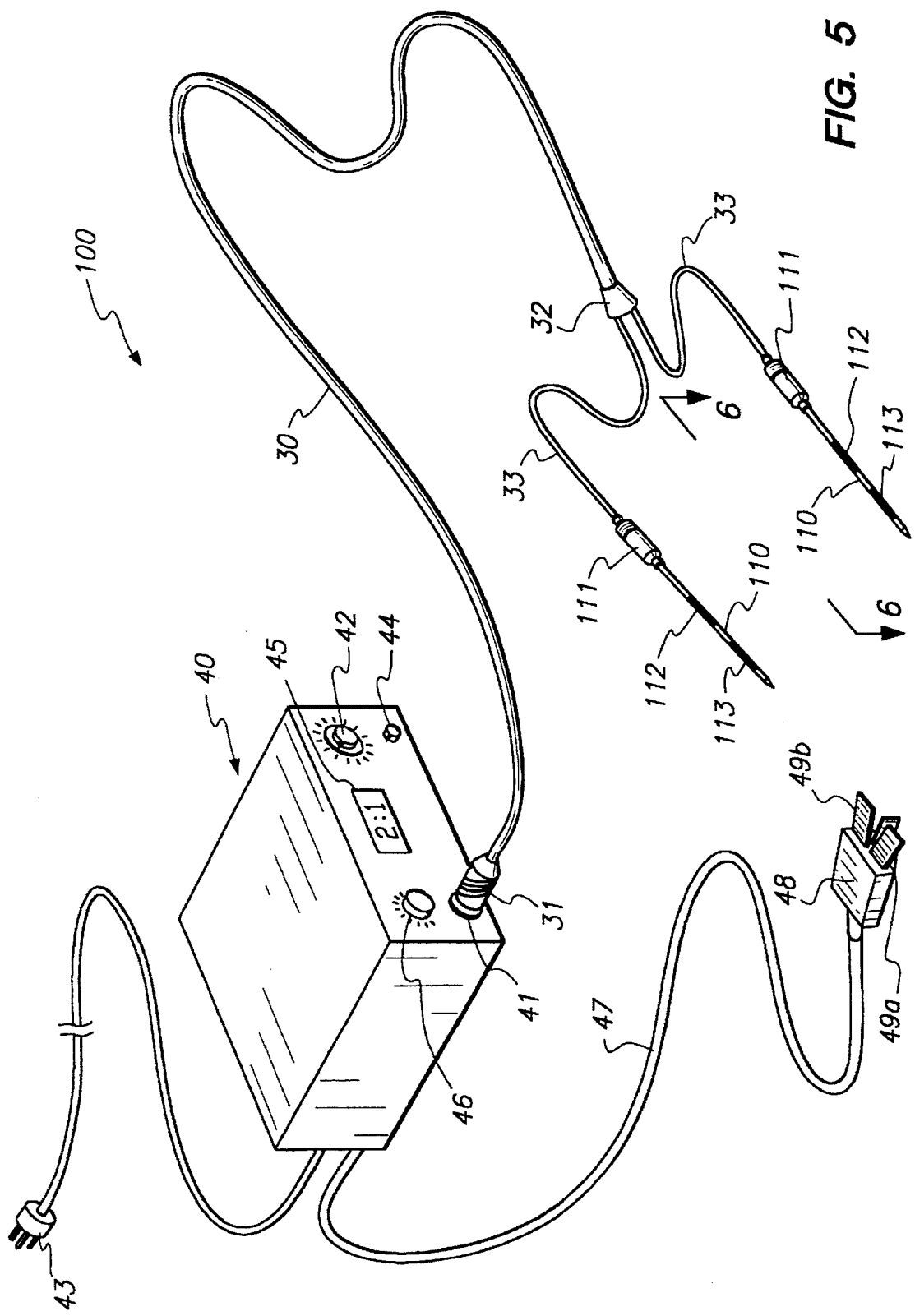
FIG. 5 is a perspective view of an alternative illustrative embodiment of the measurement and treatment probe, the control system, and connecting cable of the present invention.

Referring now to FIG. 5, a second illustrative embodiment of apparatus 100 of the present invention is described. Like components of apparatus 100 are designated with like numbers as apparatus 10 of FIG. 1. Thus, for example, cable 30 and controller 40 of the system of FIG. 5 are essentially the same as described above with respect to FIG. 1, except that diagnostic and therapeutic modes of operation are activated by footpedal 48 coupled to controller 40 via cable 47.

Apparatus 100 may provide certain advantages relative to the first-described embodiment in that it includes two measurement and treatment probes 100, which may be inserted into normal biological tissue adjacent to a suspected tumorous region. Apparatus therefore provides the capability to characterize the suspected tumor, without creating a risk of seeding the needle track with cancerous cells, as could conceivably occur with the single probe design of the first embodiment.

Measurement and treatment probes 110 of apparatus 100 are coupled to cable 30 via connector 32. Measurement and treatment probes 110 (hereinafter, the "probes") are identical and similar in design to measurement and treatment probe 20, described above. Each of probes 110 includes a hand-engagable body 111, and a removably connected support member 112. Support members 112 are similar in design and construction to support member 50 described above with respect to FIG. 2. Distal portions 113 of support members 112 carry two or more electrodes for use in the measurement of an electromagnetic property (e.g., electrical impedance) and application of heating current to the biological tissue.

Probes 110 are connected to controller 40 via cable 30. Cable 30 is divided into two (or more) cable branches 33 distally of connector 32 to provide connection to handles 111. Cable 30 includes the conducting leads necessary for the transmission of measurement signals and heating currents between controller 40 and probes 110, and may include suitable connectors at its ends so that cable 30 may be resterilized and reused multiple times.

Figure 6:
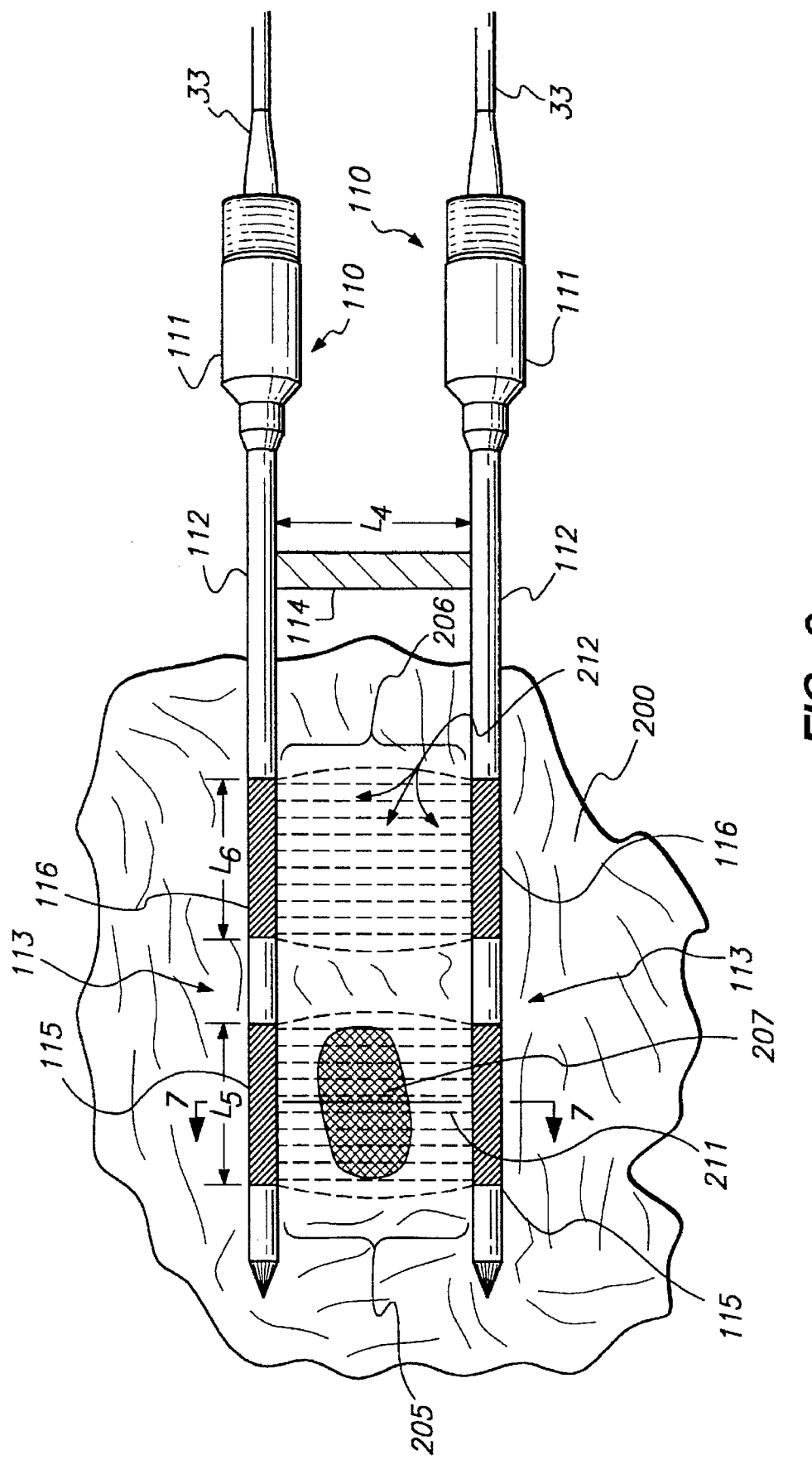
FIG. 6 is a top view of the measurement and treatment probe of FIG. 5, taken along line 6—6 of FIG. 5, showing the probe inserted into biological tissue during the measurement mode of the apparatus.

Referring now to FIG. 6, probes 110 of the second illustrative embodiment are described in greater detail. Similar to probe 20 described above, probes 110 may have support members 112, removably connected to handles 111, and may be disposable. Support members 112 have lengths and diameters suitable for allowing access to tumors in the human body, for example, diameters of about 1 mm and lengths of 10 cm or longer. Support members 111 may be connected by bridge 114 so that they lie in a common plane. Bridge 114 may have an adjustable length $L_4$ between support members 112.

Electrodes 115 and 116 are positioned along distal portions 113 of each of support members 112. During diagnostic operation of apparatus 100, an electromagnetic property of tissue in region 205 (e.g., electrical impedance) is measured by passing a sense current from electrode 115 of a first probe 110 to electrode 115 of a second probe 110, while an electromagnetic property of tissue in region 206 is measured by passing a sense current through electrodes 116 of the respective probes 110. These sense currents are illustrated by flux lines 211 and 212, respectively, in FIG. 6.

As for probe 20 described above, the voltage and current passed through tissue in regions 205 and 206 during the diagnostic mode is sufficiently low to prevent any significant heating of tissue located between the electrode pairs 115 and 116 (e.g., voltage generally less than 10 volts at frequencies between 20 kHz and 10 MHz). During a therapeutic mode of operation of apparatus 100, higher voltages and currents are supplied to electrodes 115 of the first and second probes 110, thereby causing cauterization of tissue in region 205, including the tumor 207.

Operation of the apparatus of FIGS. 5 and 6 is accomplished using footpedals 49a and 49b. In particular, footpedal 49a replaces manual measurement control 25 of probe 20 (see FIG. 1) and is used to activate the diagnostic mode of operation of apparatus 100, while footpedal 49b replaces manual therapy control 26 during the therapeutic mode of operation.

During a diagnostic mode of operation, distal ends 113 of probes 110 are inserted into the patient percutaneously and in close proximity with tumor 207. As described above, this insertion step may be guided using coordinates, tumor size and orientation determined in previous X-radiographic, sonographic and/or other diagnostic imaging procedures. Footpedal 49a is depressed to activate measurement of the electromagnetic property of tumor 207 in region 205 and of adjacent normal tissue in region 206. As described with respect to the embodiment of FIG. 1, an indication of either a measured value of an electromagnetic property or a ratio of such properties is provided by sensory display 45 to enable the characterization of the suspected tumor 207 allowing the user to address whether tumor 207 is appropriate for treatment.

The operator then releases footpedal 49a and withdraws probes 110 from the patient's tissue or, if the assessment indicates the suspected tumor 207 should be treated, depresses footpedal 49b until the desired tissue treatment (e.g., cauterization) is accomplished. The duration of the application of heating current to the biological tissue in region 205 may be selected based on a number of factors, for example, a measured period of time or level of current flowing between electrodes 115 for a given applied voltage. Probes 110 may be withdrawn when application of the therapeutic current has been completed. Alternatively, the diagnostic mode of operation may be repeated following application of the therapeutic current to assess the degree of necrosis induced in the tissue.

Applicants expect that heating of tissue 200 and tumor 207 in region 205 will cause not only the desired cauterization of tissue in region 205, but will also cause an increase in the electrical impedance of tissue in region 205. Thus, for a fixed (constant) level of applied voltage between electrodes 115, the level of electrical current flowing will decay as the cauterization of tissue 200 and tumor 207 proceeds. Applicants therefore expect that adequate cauterization of the tissue in region 205 will result in the electrical current level falling to a low and relatively constant value, at which time application of heating power to the tissue may be terminated.

Thus, in addition to the use of a thermistor to determine completeness of cauterization as described with reference to the embodiment of FIG. 1, applicants expect that another method of making this determination may involve monitoring the above-described fall off in electrical current supplied to probes 110 during the therapeutic mode of operation. For example, the decay of the electrical current level and the attainment of an adequate thermal treatment may be represented by an audible tone having a frequency (pitch) indicative of the level of the electrical current flowing between electrodes 115.

Figure 7:
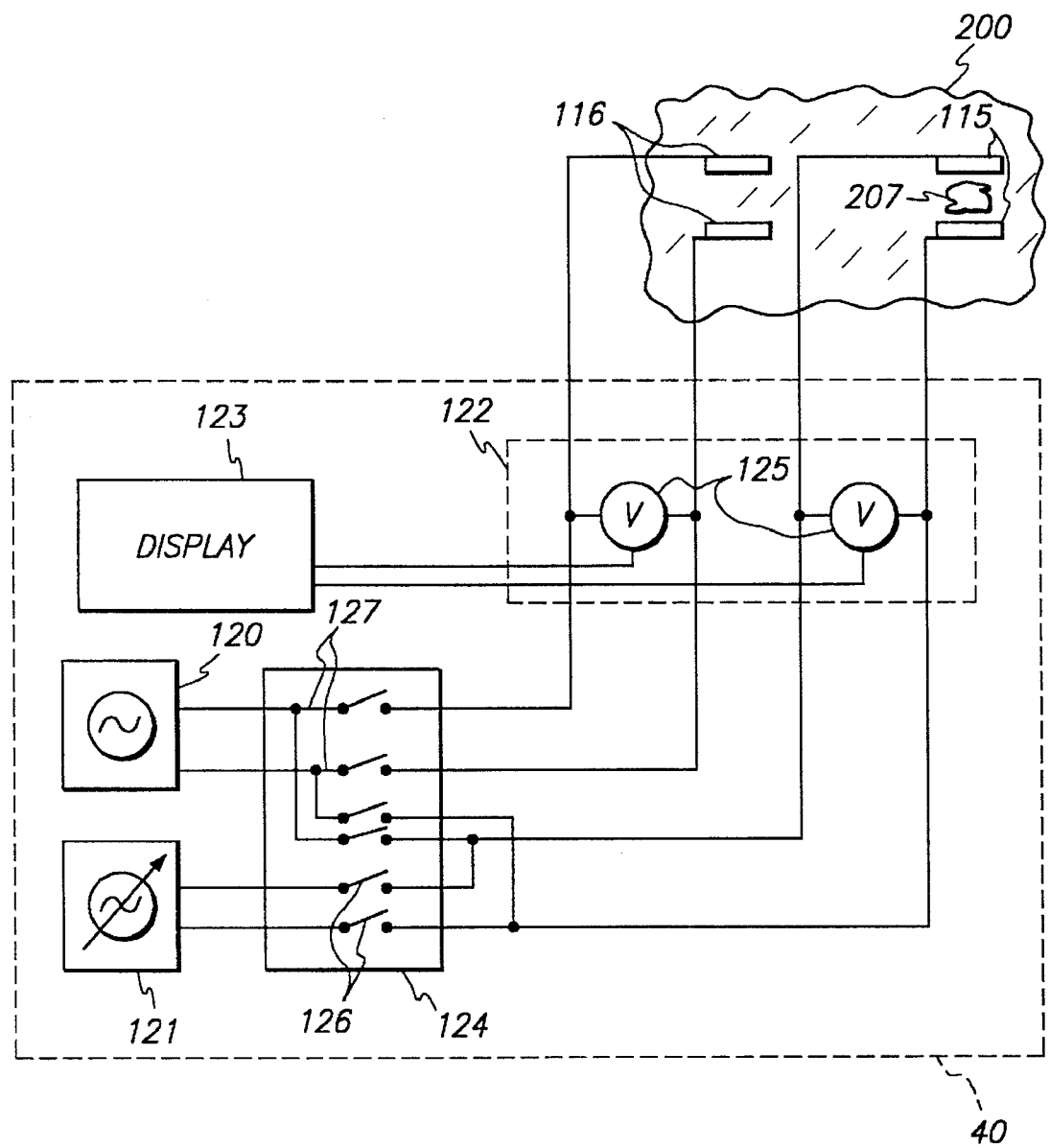
FIG. 7 is an illustrative schematic diagram of an embodiment of measurement and treatment circuitry constructed in accordance with the present invention.
Figure 8:
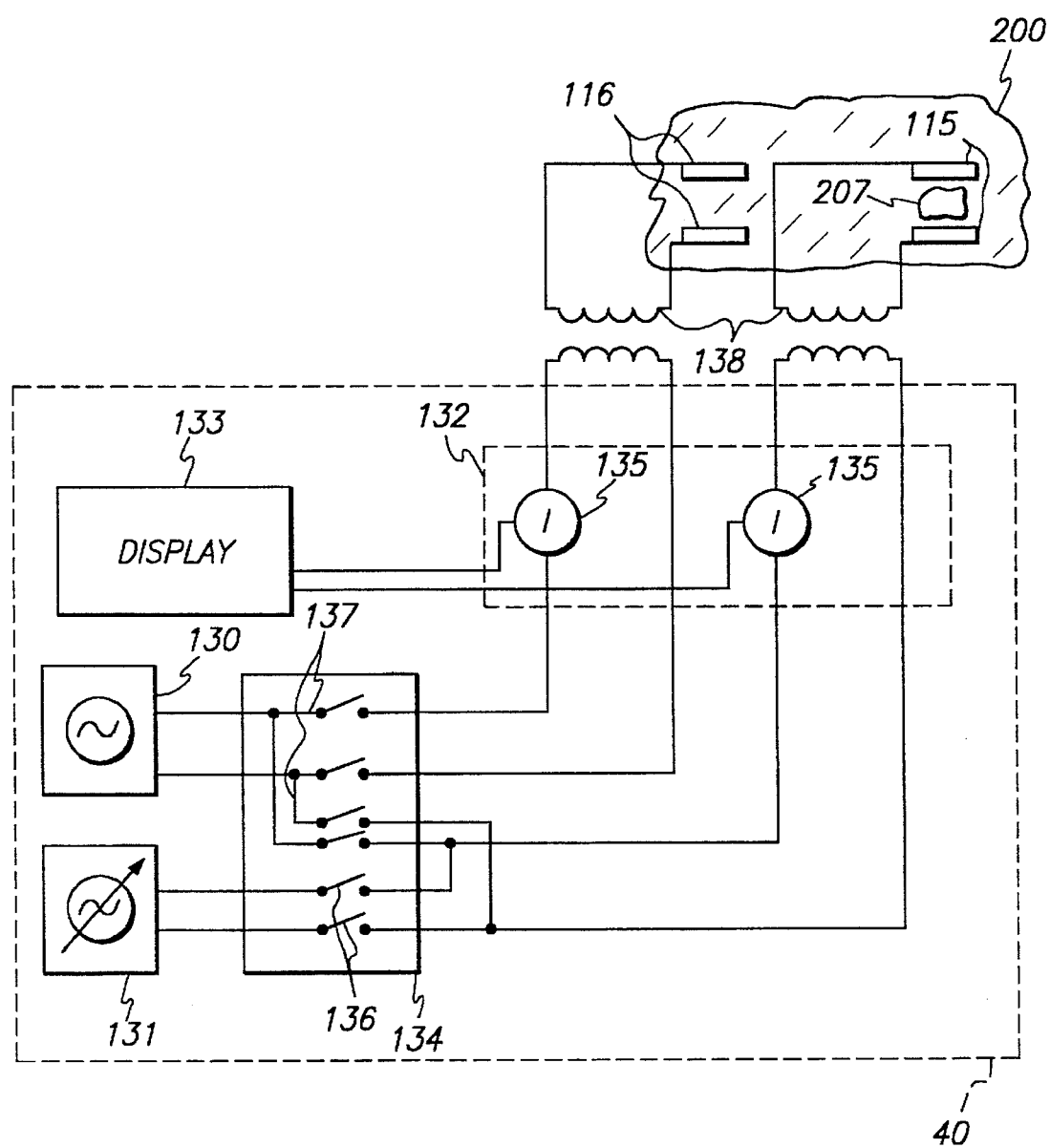
FIG. 8 is an illustrative schematic diagram of an alternative embodiment of measurement and treatment circuitry constructed in accordance with the present invention.

Referring now to FIGS. 7 and 8, embodiments of controller 40 of the present invention are described for use with apparatus 10 and 100. In accordance with the illustrative embodiments of apparatus 10 and 100 described hereinabove, in which an electrical property of the tissue is measured followed by inducing cauterization of the tissue by passing electric current through it, controller 40 includes both circuitry for measuring at least one electromagnetic property of biological tissue during a diagnostic mode of operation and circuitry for generating a radio-frequency voltage during a therapeutic mode of operation. While circuitries for performing these functions individually are per se known, illustrative arrangements suitable for use with apparatus 10 and 100 of the present invention are provided.

FIG. 7 shows a first illustrative embodiment of controller 40 (in combination with electrodes as in apparatus 100) including constant low-current power supply 120, adjustable voltage level power supply 121, sense circuitry 122, display circuitry 123, and switching circuitry 124. Constant low-current power supply 120 supplies a low voltage (less than 10 volts RMS) constant low current to electrodes 115 and 116 of apparatus 100 during the diagnostic mode of operation of apparatus 100, such that tissue 200 in the vicinity of electrodes 115 and 116 preferably experiences no more than a 2°–4° C. increase in temperature. Power supply 120 may operate at a single radio-frequency in the range 20 kHz to 10 MHz, or to account for inductance and capacitance effects of the tissue, may sample the electromagnetic property of the tissue at a number of different frequencies within that range.

Sense circuitry 122 measures the resulting voltage differences between each of electrode pair 115 and electrode pair 116, using for example, voltmeter circuitry 125 or bridge circuitry. If the measurement is performed at multiple frequencies, suitable averaging circuitry may also be employed for processing the samples. A ratio of the measured voltages may then be computed and displayed by display circuitry 123 using suitable analog or digital circuitry.

Once the operator has assessed the measured values during the diagnostic mode of operation, the operator may then actuate apparatus 100 to enter a therapeutic mode of operation, for example, by depressing footpedal 49b (see FIG. 5). Actuation of the therapeutic mode causes switching circuitry 124 to couple electrode pair 115 to adjustable voltage level power supply 121 via contacts 126, while electrode pair 116 is open-circuited.

Power supply 121 provides a radio-frequency voltage (e.g., 10–100 volts RMS at between 100 kHz and 1 MHz, and preferably 200–500 kHz) to electrodes 115 for a suitable time period, for example, 10 seconds, to cause adequate necrosis of target tissue 207. The output voltage of power supply 121 is preferably independent of the load impedance. As described above, the operator may then move between diagnostic and therapeutic modes of operation of apparatus 100 to evaluate or monitor the progress of the tissue treatment (i.e., cauterization of the tissue).

Referring to FIG. 8, an alternative embodiment of controller 40 (in combination with electrodes as in apparatus 100) of the present invention is described. Controller 40 of FIG. 8 includes constant low-voltage power supply 130, adjustable voltage level power supply 131, sense circuitry 132, display circuitry 133, and switching circuitry 134. Constant low-voltage power supply 130 supplies a constant low voltage (less than 10 volts RMS), low level current to electrodes 115 and 116 of apparatus 100 during the diagnostic mode of operation of apparatus 100.

As for the embodiment of FIG. 7, the power supplied by power supply 130 is such that tissue 200 in the vicinity of electrodes 115 and 116 preferably experiences no more than a 2°–4° C. increase in temperature. Power supply 130 may operate at a single radio-frequency in the range 20 kHz to 10 MHz, or sweep through that range to sample the tissue property at multiple frequencies.

Sense circuitry 132 measures the resulting current levels between each of electrode pair 115 and electrode pair 116 using, for example, suitable current meter circuitry 135. If the measurement is performed at multiple frequencies, suitable averaging circuitry may also be employed for processing the samples. A ratio of the measured currents may then be computed and displayed by display circuitry 133 using suitable analog or digital circuitry. This embodiment may yield more accurate tissue impedance measurements then the embodiment of FIG. 7 since the current signals conducted between electrode pairs 115 and 116 may be less sensitive to tissue inductance and capacitance.

Power supply 131 and switching circuitry 134 may then be actuated by the operator's causing apparatus 100 to enter a therapeutic mode of operation, for example, by depressing footpedal 49b. Actuation of the therapeutic mode causes switching circuitry 134 to couple electrode pair 115 to adjustable voltage level power supply 131 via contacts 136, while electrode pair 115 is open-circuited. Power supply 121 then operates to provides a suitable radio-frequency voltage to electrodes 115, as described above, to cause adequate necrosis of target tissue 207. Isolation transformers 138 may also be provided to ensure that no low-frequency leakage currents are conducted to tissue 200.

Alternatively, circuitry for measuring the electrical impedance of biological tissue as described, for example, in the above-mentioned Morimoto reference and U.S. Pat. No. 5,069,223, or circuitry for measuring the dielectric constants of biological tissue, such as found, for example, in U.S. Pat. Nos. 4,458,694 and 4,291,708, may be used in controller 40. Treatment circuitry for heating of biological tissue, such as is described, for example, in U.S. Pat. Nos. 4,016,886 and 4,121,592 may also be employed.

Illustrative embodiments 10 and 100 of the present invention provide a significant advantage over previously known measurement and treatment devices by providing both diagnostic and therapeutic capabilities in a single instrument. In particular, because the electrodes used for sensing the properties of the tumor during the diagnostic mode and treating the tumor during the therapeutic mode are located at known distances along the probes 20 and 110 (and in some cases are the same electrodes), the operator can achieve precise registration of the electrodes relative to the tumor during these two modes of operation. Such precise registration would be unachievable with previously known instruments, where a first measuring instrument and a second treatment instrument are required.

A further advantage of the probe of the present invention relates to the ability to iterate between treatment and measuring modes of operation. Thus, for example, a operator may be able to treat several tissue regions through a single incision in a serial manner, operating the instrument in diagnostic mode and then in therapeutic mode at first location in the patient's tissue. Following treatment at the first location, the operator may then move probe 20 (or probes 110) to a new position and repeat the procedure. Alternatively, even after having performed partial cauterization of a tumor, the operator might choose to measure the electrical property for a treated region to confirm the extent of the tissue treatment, followed by resumed treatment, thus alternating between diagnostic and treatment modes at a single location.

Applicants also contemplate that the electrical impedance of the tissue, or other property, be measured at two or more radio-frequencies to provide additional data for use in assessing the malignancy of a tumor. In an alternative embodiment of the present invention, apparatus 10 and 100 may be used to measure the dielectric constant of biological tissue to differentiate between malignant and nonmalignant tumors, assess degree of malignancy, or differentiate between tumors and normal tissue rather than electrical impedance.

In yet another embodiment, therapeutic treatment of a tumor suspected to be malignant using measurement apparatus and methods described above may alternatively or additionally include the use of ionizing radiation such as the miniature X-ray therapy apparatus described in U.S. Pat. Re 34,421. As yet a further alternative, tumor necrosis may be achieved by exposing the targeted tissue to cryogenic temperatures, for example, as described in U.S. Pat. No. 4,140,109.

While preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. Apparatus for in situ diagnosis and treatment of biological tissue comprising:
   a probe comprising an elongate member including first and second electrodes, the probe having a first mode of operation in which a parameter indicative of a property of a biological tissue is sensed to enable differentiation among normal biological tissue, malignant tumorous biological tissue, and nonmalignant tumorous biological tissue, and a second mode of operation causing in situ necrosis of the biological tissue;
   first circuitry coupled to the first electrode for sensing the parameter during the first mode of operation;
   second circuitry coupled to the second electrode for inducing necrosis of the biological tissue during the second mode of operation; and
   means for coupling the probe to the first and second circuitries.

2. Apparatus as defined in claim 1 wherein the elongate member has a distal end and a proximal end and the first and second electrodes are disposed axially at intervals between the distal end and the proximal end.

3. Apparatus as defined in claim 2 wherein the second circuitry induces necrosis of the biological tissue by supplying a voltage to the second electrode.

4. Apparatus as defined in claim 2, wherein the first and second electrodes comprise a material selected from the group consisting of platinum, silver, gold, stainless steel, and other biocompatible electrically conductive materials.

5. Apparatus as defined in claim 1 wherein the probe further comprises a switch for selectively activating either the first or second modes of operation.

6. Apparatus as defined in claim 1 further comprising:
   a user interface for providing a sensory indication of the sensed parameter.

7. Apparatus as defined in claim 6 wherein the user interface provides a sensory indication, during the first mode of operation, corresponding to a degree of vascularity of the biological tissue to enable characterization of the degree of malignancy.

8. Apparatus as defined in claim 6, wherein the user interface comprises a visual display or an auditory device.

9. Apparatus as defined in claim 1, wherein the parameter indicative of a property of the biological tissue is selected from the group consisting of electrical impedance and dielectric constant.

10. Apparatus as defined in claim 1 wherein the probe includes a third electrode coupled to the first circuitry and a fourth electrode coupled to the second circuitry.

11. A probe for use in situ diagnosis and treatment of biological tissue comprising:
    a handle;
    a support member removably connected to the handle;
    a plurality of electrodes, disposed on the support member, for sensing a parameter indicative of a property of a biological tissue to enable differentiation among normal biological tissue, benign tumorous biological tissue, and malignant tumorous biological tissue; and
    disposed from the support member, means for causing in situ necrosis of the biological tissue.

12. Apparatus as defined in claim 11 further comprising a user interface to provide a sensory indication corresponding to a degree of vascularity of the biological tissue to enable characterization of the degree of malignancy.

13. A probe as defined in claim 11 further comprising a switch, operatively coupled to the plurality of electrodes and the means for causing in situ necrosis, for selectively activating either the plurality of electrodes for sensing or the means for causing in situ necrosis.

14. A probe as defined in claim 13 wherein the means for causing in situ necrosis comprises a subset of the plurality of electrodes.

15. A probe as defined in claim 13, wherein the electrodes comprise a material selected from the group consisting of platinum, silver, gold, stainless steel, and other biocompatible electrically conductive materials.

16. A method for in situ diagnosis and treatment of biological tissue comprising a series of steps of:
    positioning a probe relative to a biological tissue in situ;
    actuating the probe to sense a parameter indicative of a property of the biological tissue to enable differentiation among normal biological tissue, malignant tumorous biological tissue, and nonmalignant tumorous biological tissue;
    characterizing a region of the biological tissue based upon the sensed parameter; and
    selectively actuating the probe to cause necrosis of the region of biological tissue.

17. The method of claim 16 wherein the step of characterizing comprises assessing the degree of malignancy of the region.

18. The method of claim 16, wherein the parameter is selected from a group consisting of electrical impedance and dielectric constant.

19. The method of claim 16, wherein the step of sensing measures the electrical impedance of the biological tissue at one or more frequencies in the range of 20 kHz to 20 MHz.

20. The method of claim 16, wherein the step of selectively actuating the probe to cause necrosis induces elevated temperatures in the region of biological tissue.

21. The method of claim 20, wherein the elevated temperatures are in a range of 60° C. to 100° C.

22. The method of claim 20, wherein elevated temperatures are induced by passing a radio-frequency electric current through the biological tissue, the electric current having a frequency in a range 100 KHz to 1 MHz.

23. A probe for use in situ diagnosis and treatment of biological tissue comprising:

a handle;

a support member removably connected to the handle;

at least one electrode, disposed on the support member, for sensing a parameter indicative of a property of a biological tissue to enable differentiation among normal biological tissue, benign tumorous biological tissue, and malignant tumorous biological tissue; and disposed from the support member, means for causing in situ necrosis of the biological tissue.

24. Apparatus as defined in claim 23 further comprising a user interface to provide a sensory indication corresponding to a degree of vascularity of the biological tissue to enable characterization of the degree of malignancy.

25. A probe as defined in claim 23 further comprising a switch, operatively coupled to the at least one electrode and the means for causing in situ necrosis, for selectively activating either the at least one electrode for sensing or the means for causing in situ necrosis.

26. A probe as defined in claim 23, wherein the at least one electrode comprises a material selected from the group consisting of platinum, silver, gold, stainless steel, and other biocompatible electrically conductive materials.

27. Apparatus for in situ diagnosis and treatment of biological tissue comprising:

a first probe comprising an elongate member including a first electrode and a second probe comprising an elongate member including a second electrode, the first and second probes having a first mode of concurrent operation in which a parameter indicative of a property of a biological tissue is sensed to enable differentiation among normal biological tissue, malignant tumorous biological tissue, and nonmalignant tumorous biological tissue, and a second mode of concurrent operation causing in situ necrosis of the biological tissue;

first circuitry coupled to the first and second electrodes for sensing the parameter during the first mode of concurrent operation;

second circuitry coupled to the first and second electrodes for inducing necrosis of the biological tissue during the second mode of concurrent operation; and means for coupling the first and second probes to the first and second circuitries.

28. Apparatus as defined in claim 27 wherein the first probe includes a third electrode coupled to the first circuitry and the second probe includes a fourth electrode coupled to the first circuitry.

29. Apparatus as defined in claim 27 further comprising a switch operatively coupled to the first and second circuitries for selectively activating either the first or second modes of concurrent operation.

30. Apparatus as defined in claim 27 further comprising a user interface for providing a sensory indication of the sensed parameter.

31. Apparatus as defined in claim 30 wherein the user interface provides a sensory indication, during the first mode of concurrent operation, corresponding to a degree of vascularity of the biological tissue to enable characterization of the degree of malignancy.

32. Apparatus as defined in claim 30, wherein the user interface comprises a visual display or an auditory device.

33. Apparatus as defined in claim 27, wherein the parameter indicative of a property of the biological tissue is selected from the group consisting of electrical impedance and dielectric constant.

34. Apparatus as defined in claim 27 wherein the second circuitry induces necrosis of the biological tissue by supplying a voltage to the first and second electrodes.

35. Apparatus as defined in claim 27, wherein the first and second electrodes comprise a material selected from the group consisting of platinum, silver, gold, stainless steel, and other biocompatible electrically conductive materials.

* * * * *